United States Patent [19]

Lashinski

[11] Patent Number: 5,185,004
[45] Date of Patent: Feb. 9, 1993

[54] TURN-LIMITING PROXIMAL ADAPTOR FOR STEERABLE CATHETER SYSTEMS

[75] Inventor: Robert Lashinski, Elk River, Minn.

[73] Assignee: Danforth Biomedical, Inc., Menlo Park, Calif.

[21] Appl. No.: 709,572

[22] Filed: Jun. 3, 1991

[51] Int. Cl.[5] ............................................. A61M 37/00
[52] U.S. Cl. .................................... 604/95; 604/280; 128/657
[58] Field of Search ................. 128/656–658, 128/772; 604/95–96, 280

[56] References Cited

U.S. PATENT DOCUMENTS

| | | |
|---|---|---|
| Re. 33,166 | 2/1990 | Samson . |
| 4,573,470 | 3/1986 | Samson et al. . |
| 4,582,181 | 4/1986 | Samson . |
| 4,619,263 | 10/1986 | Frisbie et al. . |
| 4,664,113 | 5/1987 | Frisbie et al. ............... 604/96 X |
| 4,715,378 | 12/1987 | Pope, Jr. et al. . |
| 4,723,936 | 2/1988 | Buchbinder et al. . |
| 4,793,350 | 12/1988 | Mar et al. ............... 604/96 X |
| 4,898,577 | 2/1990 | Badger et al. ............... 604/53 |
| 4,955,384 | 9/1990 | Taylor et al. . |
| 5,002,560 | 3/1991 | Machold et al. ............... 606/198 |
| 5,055,109 | 10/1991 | Gould et al. ............... 604/95 |
| 5,114,403 | 5/1992 | Clarke et al. ............... 604/96 |

Primary Examiner—C. Fred Rosenbaum
Assistant Examiner—C. Maglione
Attorney, Agent, or Firm—Townsend and Townsend

[57] ABSTRACT

A turn-limiting proximal adaptor for steerable catheter systems comprising a stationary portion and a rotator portion, the rotator portion secured to a guidewire to provide rotational mobility of the guidewire component relative to the catheter component. The proximal adaptor includes a turn-limiter section which has a translational nut threaded onto a central element and limited in longitudinal displacement by a proximal stop and a distal stop. The central threaded element is secured to the stationary portion of the proximal adapter and forms a torsionally rigid body. The translational nut and threaded central element are enclosed within a rotator which is rotatably mounted to said stationary portion and is affixed to the guide wire such that when the rotator is rotated, the guide wire rotates and the translational nut rotates about the threaded central element, in rotational communication with the rotator, and moves in the longitudinal direction until it is stopped by the distal stop means or the proximal stop means. The turn-limiting section is transparent to allow the user to view the rotational displacement of the guide wire by the corresponding longitudinal movement of the translational nut.

10 Claims, 2 Drawing Sheets

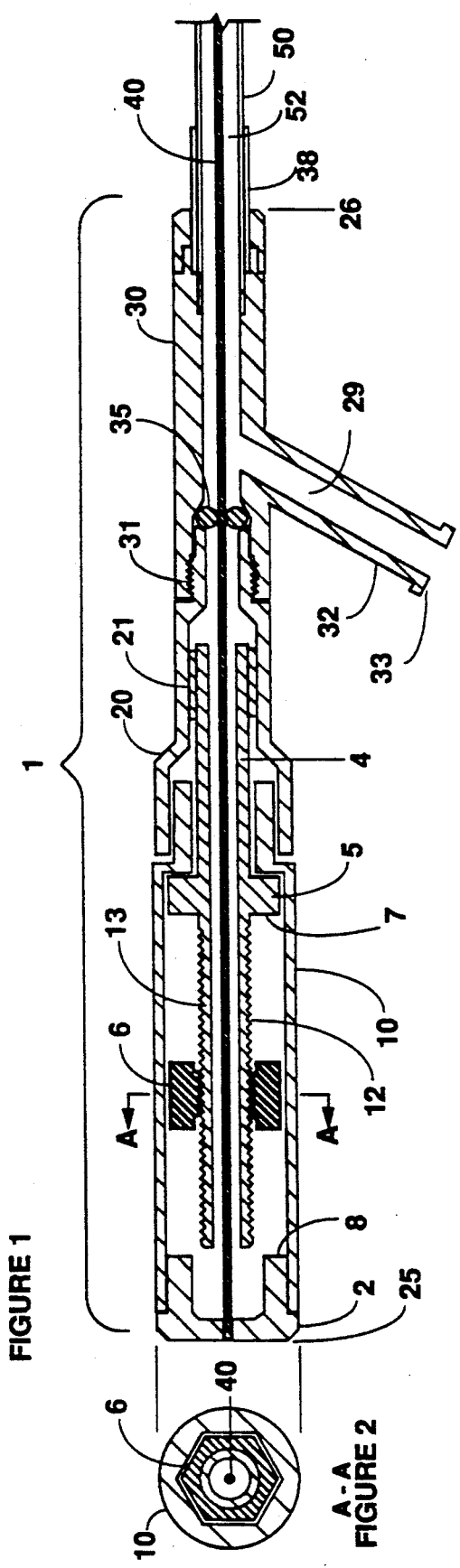
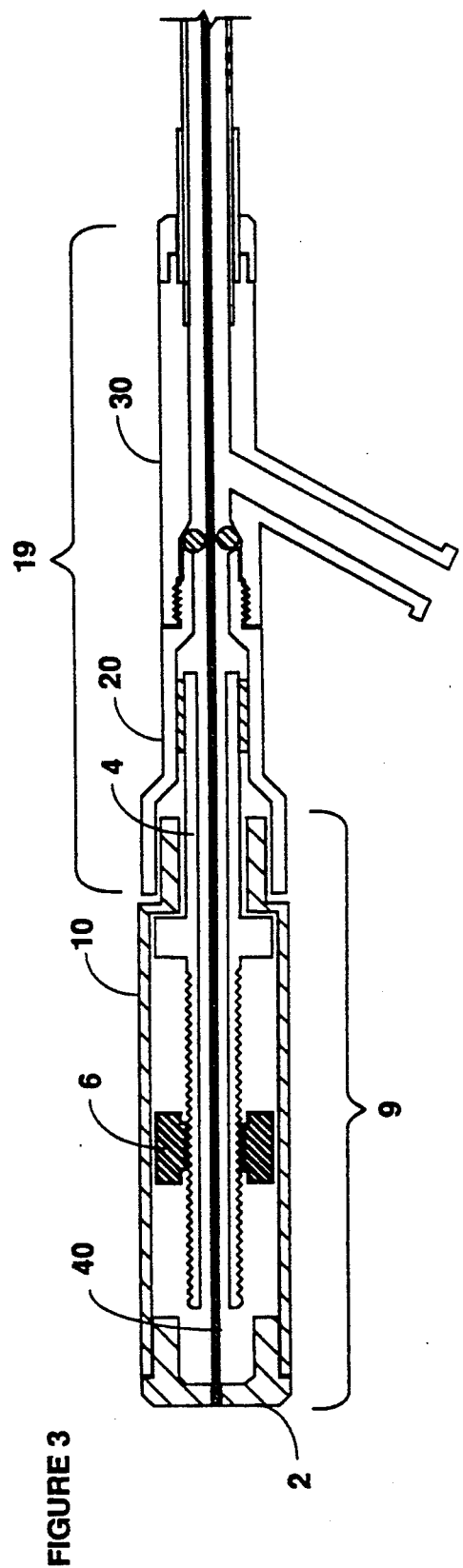

TURN-LIMITING PROXIMAL ADAPTOR FOR STEERABLE CATHETER SYSTEMS

BACKGROUND OF THE INVENTION

This invention relates to steerable catheter-guidewire systems, more particularly to turn-limiters for steerable guidewire-directed catheter system, including "fixed-wire" angioplasty dilation balloon catheter-guidewire systems.

Steerable guidewire-directed catheter systems are systems that contain movable guidewire components. Directional control of these systems is accomplished by rotating, advancing, and/or retracting the guidewire components relative to the catheter components of these systems. Typically, the facility with which a steerable guidewire-directed catheter system can be advanced within the confines of a tortuous lumen varies as a function of the mobility of the guidewire component relative to the catheter component of the particular system. "Fixed-wire" angioplasty dilatation balloon catheter systems are steerable guidewire-directed catheter systems that are used to accomplish percutaneous transluminal balloon-mediated dilatation of intravascular lesions. Typically, "fixed-wire" angioplasty balloon catheter systems permit the performance of an angioplasty within the confines of lesions that frequently cannot accommodate "over-the-wire" systems. For example, U.S. Pat. No. 4,582,181 describes a "fixed-wire" angioplasty dilatation balloon catheter-guidewire system. These systems comprise, in general, a catheter component (composed, at least, of a proximal adapter, catheter shaft, and dilatation balloon) and a guidewire component (composed, at least, of a mandrel and a tip coil). "Fixed-wire" angioplasty catheter-guidewire systems are distinguished from other angioplasty systems by virtue of the mobility of the guidewire component relative to the catheter component of these systems. Specifically, "fixed-wire" systems afford variable rotational catheter-guidewire intercomponent mobility. However, these devices do not provide any corresponding coaxial catheter-guidewire inter-component mobility. Other things being equal, the directional control or "steerability" of a "fixed-wire" system varies directly with the rotational mobility of the guidewire component relative to the catheter component.

The construction of a hydraulically competent, single-channel "fixed-wire" angioplasty system requires the creation of a liquid-tight seal between the catheter and guidewire component at the distal catheter/-guidewire interface. With many single-channel "fixed-wire" catheter systems of the prior art, adhesives have been typically used to create this interface. This approach effectively joins the balloon and guidewire components within the distal catheter/guidewire interface. As examples, U.S. Pat. Nos. 4,573,470, 4,582,181, 4,664,113, 4,715,378, 4,723,936, 4,793,350, 4,955,384 and Re 33,166 describe "fixed-wire" systems containing adhesive seals.

The practice of joining the catheter component to the guidewire component, in the construction of these systems, subjects the balloon and guidewire components to shear forces during uni-directional rotation of the guidewire components relative to the catheter components. Excessive uni-directional rotation of the guidewire components relative to the catheter components predisposes these systems to the development of balloon wrapping, balloon rupture and guidewire fracture. In general, these systems tolerate less than 5–8 uni-directional guidewire revolutions for this reason.

Turn limiters have been developed to limit the number of uni-directional turns that can be applied to the guidewire components of "fixed-wire" angioplasty catheter-guidewire systems, and to prevent the development of structural damage to these systems due to excessive uni-directional guidewire rotation. For example, U.S. Pat. No. 4,664,113 describes a rotation or turn limiter, the functional mechanism of which is comprised of a stack of inter-locking discs. Each disc contains a groove and an arresting pin. The groove of one disc is designed to receive the arresting pin of the adjacent disc. U.S. Pat. No. 4,619,263 describes a turn limiter device which uses a rotational torque knob to drive the guidewire, the torque knob threading into and out of a thumb screw. The torque knob includes arms which functionally limit the longitudinal distance the torque knob can travel, thereby limiting the rotation of the guidewire. This structure causes the guidewire to move longitudinally as it rotates, due to the translation of the torque knob.

The above turn-limiters were developed specifically for use in conjunction with "fixed-wire" devices that accommodate less than 4–5 uni-directional revolutions of the guidewire components relative to the catheter components. These prior art turn limiters complicate the angioplasty procedure because they commonly require the operator to periodically stop the procedure and unwind the guidewire to its "home" position as the operator negotiates the catheter system through the convoluted arteries of the patient's cardiovascular system. Clearly, the frequency with which the operator is required to unwind a "fixed-wire" system varies inversely with the rotational capacity of the particular system, which, in turn, relates to the rotational capacity of either: (1) the catheter-guidewire interface or (2) the turn-limiter. Systems of the prior art that accommodate less than 4–5 uni-directional guidewire turns commonly provoke significant distraction to the operator. Typically, these systems provide no information to the operator regarding the rotational status of the guidewire component relative to the catheter component and hence these systems are prone to require unwinding without notice.

An advanced "fixed-wire" system capable of accommodating a considerably greater number of uni-direction guidewire rotations has been developed by Danforth BioMedical, Inc. of Menlo Park, Calif. ("DBI"), and is subject to U.S. patent application Ser. No. 615,721, filed on Nov. 19, 1990. This device affords superior directional control and provokes less interruption to the performance of the procedure relative to the prior art. The device, however, requires a turn limiter that accommodates upwards of twenty uni-directional guidewire revolutions.

No prior art turn limiter is particularly suitable for use in conjunction with such an advanced fixed-wire system. The maximum number of uni-directional turns that can be accommodated by the device described in U.S. Pat. No. 4,664,113, for example, varies as a function of the number of discs that are stacked together in the construction of the mechanism. Each disc contributes less than one full revolution. Modifying this turn limiter to accommodate twenty uni-directional guidewire rotations would require stacking more than twenty interlocking discs together in the construction of the functional mechanism. Although feasible, this approach is disadvantageous in that it results in the generation of a particularly complex, multi-component, elongated device that would be expensive to manufacture and cumbersome to handle.

The operation of the turn limiter described in U.S. Pat. No. 4,619,263 causes the guidewire component to advance or retract relative to the catheter component as it is rotated. The magnitude of coaxial catheter-guidewire translation that develops in response to rotation of the guidewire component varies as a function of the number of uni-direction turns that are applied to the system. The use of this turn-limiter in conjunction with the DBI "fixed-wire" device previously described would result in significant coaxial expansion or contraction of the composite system. Therefore, the use of this turn-limiter in conjunction with a device such as the DBI device would further disrupt the spatial relationship between the proximal end of the guidewire tip coil and the distal end of the balloon component of the DBI system and thereby disrupt the surface contour of the distal catheter/guidewire transition. This circumstance, in turn, could adversely influence the surface resistance of the distal aspect of the composite system.

From the foregoing it becomes evident that the directional control of a "fixed-wire" catheter/guidewire system varies directly as a function of the rotational mobility of the guidewire component relative to the catheter component of the system. Therefore, it is foreseeable that future "fixed-wire" devices will continue to be developed to provide superior guidewire rotational mobility relative to conventional devices. Turn-limiting devices must be employed to prevent excessive uni-directional rotation of the guidewire components disposed within the catheter components of selected "fixed-wire" systems. Prior art turn limiters, however, are particularly suited for use in conjunction with devices that only tolerate less than 4-6 uni-directional guidewire rotations.

The advent of "fixed-wire" devices that afford uni-directional enhanced guidewire rotational mobility relative to the prior art create the need for turn-limiters that permit substantially greater uni-directional guidewire rotational mobility, that are easy to construct, and that do not provoke coaxial translation of the guidewire component relative to the catheter component consequent with intercomponent rotation. Hereinafter is described a turn limiter that meets these and other needs.

SUMMARY OF THE INVENTION

The invention is a turn-limiting proximal adaptor for "fixed-wire" catheter systems. The invention employs a simple mechanical construction and affords multiple advantages relative to the prior art. The simplicity of construction translates into several desirable features, such as the device: (1) can be easily adjusted to accommodate a broad rotational range; (2) can be easily and inexpensively manufactured; (3) can be visually inspected to assess the rotational status of the guidewire component relative to the catheter component; and (4) does not provoke any coaxial translation of the guidewire component relative to the catheter component of the system. In addition, the use of the present invention enables the user to perform an angioplasty procedure with greater precision, less effort and with less distraction than turn limiters of the prior art.

In the preferred embodiment of the invention, the proximal adaptor is generally constructed having a rotator portion at its proximal end and a stationary portion at its distal end. The catheter shaft is secured to the distal end of the stationary portion by a liquid-tight seal. The proximal adaptor also includes an infusion port, extending out from the stationary portion, that communicates with the hydraulic channel and permits the delivery of hydraulic fluid into the system.

The rotator portion of the proximal adaptor has a rotator cap at its proximal end. The rotator cap acts as a proximal anchor for the guidewire wherein the guidewire is fixed or bonded to the rotator cap and extends centrally through the proximal adaptor and into the catheter shaft in the proximal to distal direction. This "fixed-wire" configuration allows the user to rotate the guidewire relative to the proximal adaptor by applying rotational force to the rotator portion. The torsional rigidity of the guidewire provides close to a one-to-one correspondence between rotation of the rotator portion and rotation of the distal tip of the guidewire.

A threaded central element is bonded to the stationary portion of the proximal adaptor and extends back in the distal to proximal direction from the stationary portion. The rotator is rotatably connected to the stationary portion and rotates about the threaded central element which extends therein. A translational nut is threaded onto the threaded central element and is in rotational communication with the rotator portion of the proximal adaptor. As the rotator is rotated relative to the stationary portion, the communication between the rotator and the translational nut causes the nut to travel along the threaded central element in the longitudinal direction either in the proximal to distal or distal to proximal direction depending upon the direction of rotation.

The threaded central element includes a flange which acts as a distal stop surface limiting the longitudinal travel of the translational nut in the proximal to distal direction. Likewise, the rotator cap which is secured to the proximal end of the rotator, includes a proximal stop surface which limits the longitudinal travel of the translational nut in the distal to proximal direction. These stop surfaces act to limit the number of turns which can be applied to the guide wire. The rotator, being in rotational communication with the translational nut, can only rotate when the translational nut can rotate. The translational nut can only rotate about the threaded central element between the proximal stop surface and the distal stop surface. Therefore, the number of rotations which can be applied to the guidewire by the rotator is dictated by the number of rotations the translational nut travels as it threads along the threaded central element between the stop surfaces.

The proximal adaptor can be fabricated to accommodate a wide range of rotation limits by simply changing the length and/or the number of threads of the threaded central element or the pitch of the threads.

In the preferred embodiment of the invention, the rotator portion is made of translucent material. This feature allows the user to view the relative position of the translational nut on the threaded central element and its proximity to the distal stop surface and the proximal stop surface. Accordingly, the user can determine the degree of rotation of the guide wire by viewing the relative position and movement of the translational nut between the distal stop surface and the proximal stop surface.

In summary, the invention is advantageous over the prior art for several reasons. For example, the invention provides a proximal adaptor for use with "fixed-wire" catheter systems which has a turn-limiting apparatus with a broad rotational range and which allows the user to visually inspect the rotational status of the guidewire. Additionally, the functional aspects of the invention are accomplished using simple mechanical means which can be easily and inexpensively manufactured. The unique mechanical structure of the invention allows it to be constructed in various configurations to accommodate a wide range of rotation limits. The use of the device enables the user to perform an angioplasty procedure with greater precision and less effort than prior art devices while reducing the risk of trauma to the patient.

The foregoing and other aspects of the invention will become apparent from the following detailed description, illustrations and claims.

BRIEF DESCRIPTION OF THE DRAWINGS

FIG. 1 is a side view of the preferred embodiment of the invention shown in cross-section illustrating the internal components of the proximal adaptor.

FIG. 2 is a cross section of the device illustrated in FIG. 1 taken along section A—A showing a cross section of the translational nut disposed on the threaded central element and surrounded by the rotator portion.

FIG. 3 is a side view of the device illustrated in FIG. 1 illustrating the rotating components of the invention as cross-hatched and the stationary portions of the invention without cross-hatches.

DESCRIPTION OF THE PREFERRED EMBODIMENT

Figure 4:
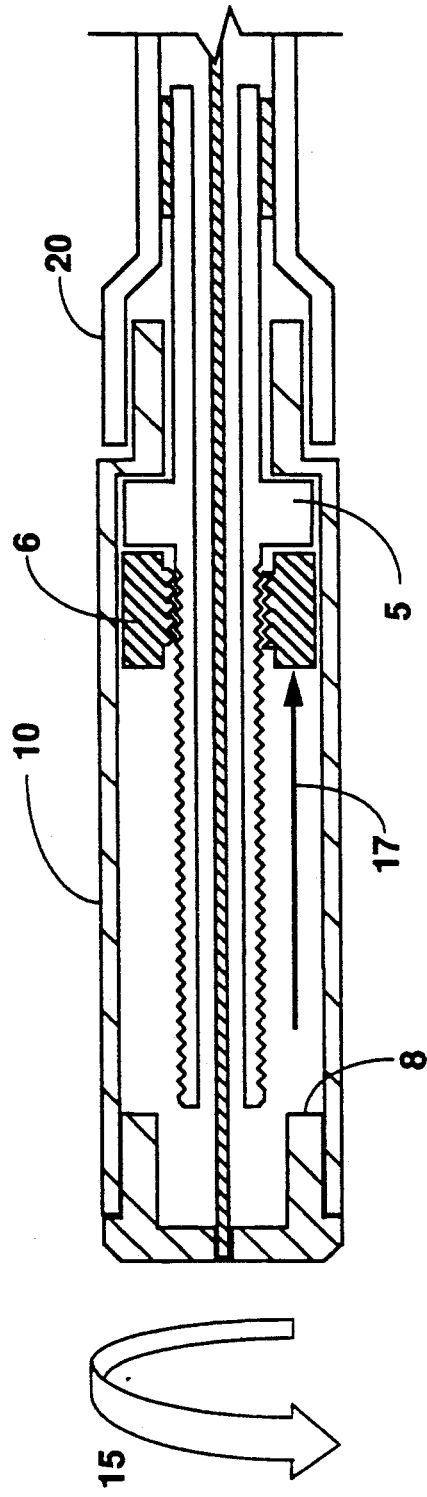
FIG. 4 is a partial side view of the proximal adaptor illustrating the relative movement of the translational nut in the proximal to distal direction until it abuts with the distal stop surface as the rotator is rotated in the counter-clockwise direction.

Referring first to FIG. 1, the invention comprises a proximal adaptor 1 having a proximal end 25 and a distal end 26. The proximal adaptor 1 is comprised of a stationary portion 19 and a turn-limiter section 9 as shown in FIG. 3. The stationary portion 19 includes a first stationary element 20 bonded to a second stationary portion 30 using a hydraulically competent bond 31. Alternatively, stationary portion 19 may be formed of a single piece of material. The distal end 26 of the proximal adaptor 1 is coupled to a catheter shaft 50 which extends from the distal end 26 of the proximal adaptor 1 a desired length in the proximal to distal direction. Catheter shaft 50 may be of any desired length and stiffness required for the particular application. Seal element 35 is disposed between stationary portions 20 and 30 to provide a hydraulically competent seal between the catheter shaft 50 and the proximal adaptor 1. Threaded central element 4 extends from the stationary portion 19 in the distal to proximal direction. The threaded central element 4 is bonded to the stationary portion 19 using hydraulically competent bonds 21 such that the threaded central element 4 is integral with the first stationary element 20 which in turn is integral with the second stationary element 30 to form a torsionally rigid body.

Threaded central element 4 has a screw 13 with threads 12 for receiving a translational nut 6 having corresponding threads about its inner surface. A flange 5 extends outwardly perpendicular to the longitudinal axis of the threaded central element 4 to create a distal stop surface 7. The screw portion 13 of the threaded central element 4 can be made of any desired length and having threads 12 of any desired pitch. Variation of the length and pitch allows a wide range of relative movement of the translational nut 6 when rotated about the screw portion 13 causing the nut 6 to travel along the longitudinal axis of the threaded central element 4.

Turn-limiter section 9 is disposed at the distal end 25 of the proximal adaptor 1. The turn-limiter section 9 includes a rotator 10 and a rotator cap 2. FIG. 2 shows a cross section of turn-limiter section 9 at line A—A of FIG. 1. As shown in FIG. 2, the rotator has an inside surface configuration to allow rotational communication between the rotator 10 and the translational nut 6. In the preferred embodiment, the translational nut 6 is of hexagonal shape and the inside surface configuration of the rotator 10 is of corresponding hexagonal shape. It is intended that the hexagonal configuration of the inside surface of the rotator 10 be slightly larger than the dimensions of the hexagonal translational nut 6. This design allows transfer of rotational force applied to the rotator 10 directly to the translational nut 6 such that when the rotator 10 is rotated, the translational nut 6 is rotated at a one to one ratio while allowing the nut 6 to travel in the longitudinal direction with minimal friction. The rotational force applied to the rotator 10 is transferred to the guide wire 40 through the rotator cap 2 causing the guide wire 40 to rotate with the rotator.

FIG. 3 shows the rotating components of the invention as cross-hatched and the stationary portions of the invention without cross-hatches. Note that the rotator 10, cap 2 and guidewire 40 rotate as a single unit, while the nut 6 translates longitudinally, in rotational communication with the rotator 10, along the screw portion 13 of the central element 4 which itself is stationary and secured to stationary portion 19.

As illustrated in FIG. 4, when the rotator is rotated in the counterclockwise direction shown by arrow 15, the communication between the rotator 10 and the translational nut 6 causes the translational nut 6 to rotate in the counterclockwise direction and travel in the proximal to distal direction along the longitudinal axis of the threaded central element 4 as shown by arrow 17. As the counterclockwise rotation shown by arrow 15 continues, the translational nut 6 will travel in the proximal to distal direction 17 until the translational nut 6 abuts with the distal stop surface 7 of the flange 5 located on the threaded central element 4. Rotator cap 2 is affixed to the proximal end 25 of the rotator 10 and provides a proximal stop surface 8.

Figure 5:
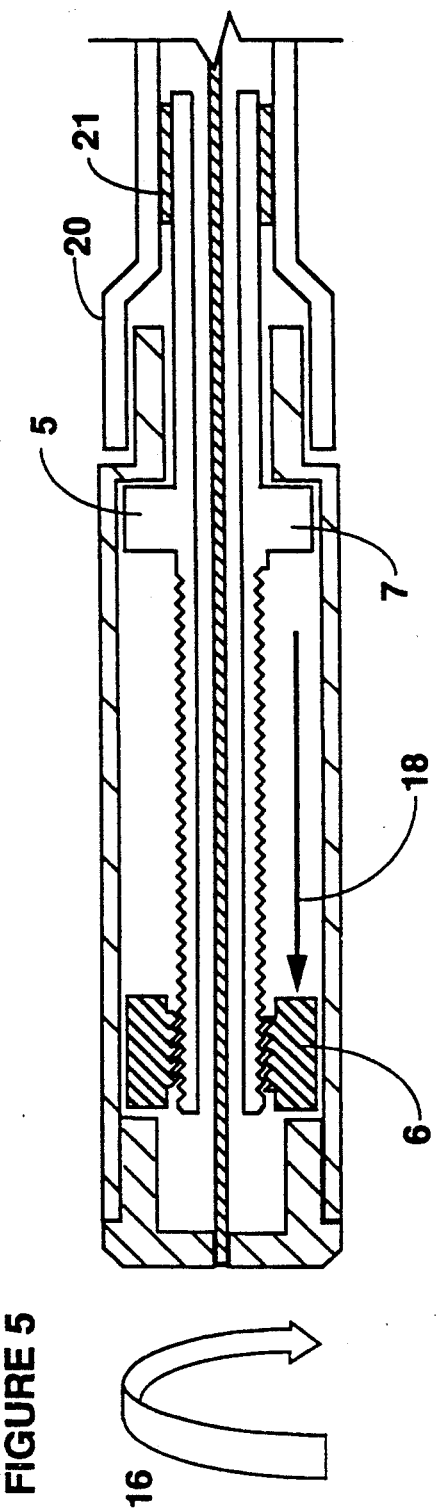
FIG. 5 is a partial profile view of the proximal adaptor illustrating the relative movement of the translational nut in the distal to proximal direction relative to the threaded central element until the translational nut abuts with the proximal stop surface of the rotator cap when the rotator is rotated in the clockwise direction.

As shown in FIG. 5, when the rotator 10 is rotated in the clockwise direction indicated by arrow 16, the clockwise rotational force is transferred from the rotator 10 to the translational nut 6 causing the translational nut 6 to travel in the distal to proximal direction indicated by arrow 18 until the translational nut 6 abuts the proximal stop surface 8 of the rotator cap 2. When nut 6 abuts either stop surface 7 or stop surface 8, nut 6 is prevented from rotating in the applicable direction and, due to the rotational contact between nut 6 and rotator 10, the rotator 10 is also prevented from rotating in that direction. This effectively limits the number of turns which can be applied to the guidewire 40.

The guidewire 40 is securely fixed to the rotator cap 2 during molding or using an appropriate adhesive. The guidewire 40, anchored in the rotator cap 2, extends in proximal to distal direction through the length of proximal adaptor 1 and into the catheter shaft 50. The integral connection between the rotator cap 2 and the guidewire 40 provides a direct transfer of all torsional forces applied on the rotator 10, thus the rotator cap 2, to the guidewire 40. As a result, the structure of the turn-limiting section 9 creates an effective transfer of all rotational forces applied to the rotator 10 directly to the guidewire 40 and limits the range of rotations available in either direction.

In the preferred embodiment, the rotator 10 is made of a translucent material, and the translational nut 6 is made of a particularly "eye-catching" colored material, such as fluorescent plastic, which in combination allows the user to view the travel of the translational nut 6 along the longitudinal axis of the threaded central element 4 as the turn-limiting section 9 is rotated. This allows the user to determine the relative number of rotations of the guide wire 40 between any two reference points dependent upon the pitch of the threads 12 and the length of the screw portion 13. By changing these two variables, the turn-limiter section 9 can be configured to restrict the maximum of turns through a large range, anywhere from one turn to as many as fifty turns.

The stationary portion 19 includes a side arm 32 which provides a flush port 29 in communication with the hydraulic lumen 52. A luer lock hub 33 is formed on the external end of the side arm 32 to facilitate a luer lock connection with an external fluid apparatus. An 0-ring 35 is positioned between the stationary portion 19 of the proximal adaptor 1 and the guide wire 40 and forms a fluid-tight seal between them. The O-ring 35 is made of a material selected to provide a very low coefficient of friction between the 0-ring 35 and the guide wire 40 as to not inhibit any torsional or rotational forces communicated to the guide wire 40 by rotation of the rotator 10. The fluid-tight seal formed by the 0-ring 35, in conjunction with the seal element 38 and the luer lock hub 33, provide an effective fluid-tight channel coupling catheter shaft 50 to flush port 29 within the side arm 32.

The foregoing description of the preferred embodiment of the invention has been presented for purpose of illustration and description. It is not intended to be exhaustive or to limit the invention to the precise form disclosed, and obviously many modifications and variations are possible in light of the above teaching without departing from the spirit of the invention. For example, the proximal adaptor 1 can be configured to accommodate a "semi-movable" catheter system, or the hexagonal shape of nut 6 and rotator 10 could be changed to square, octagon, etc. Many other modifications are possible. The embodiment chosen and described in this description was selected to best explain the principles of the invention and its practical application to thereby enable others skilled in the art to best utilize the invention in various embodiments and with various modifications are suited to the particular use contemplated. It is intended that the scope of the invention be defined by the claims appended hereto.

What is claimed is:

1. A proximal adaptor for steerable catheter systems containing a catheter shaft and a guidewire, said proximal adapter comprising:
    a stationary portion coupled to said catheter shaft;
    a rotator portion rotationally coupled to said stationary portion in a coaxial configuration, said rotator portion rotatable relative to said stationary portion without translation, said guidewire torsionally connected to said rotator portion; and
    a threaded element, coupled to said stationary portion, including threads along its outer surface,
    first and second stops positioned at opposite ends of said threaded element limiting travel along said threaded element; and
    a translational element engaged in a threaded manner with the outer surface of said threaded element between said first and second stops, said translational element further engaged with said rotator portion in a manner such that rotation of said rotator portion causes longitudinal movement of said translational element along said threaded element, said longitudinal movement limited by said first and second stops.

2. The proximal adaptor of claim 1 wherein the rotator portion includes a bore configured to receive said threaded element and said translational element, the rotator portion having an inner surface configured to abut said translational element such that rotational force applied to said rotator portion is directly communicated to said translational element.

3. The proximal adaptor of claim 2 wherein said first stop is coupled with said stationary portion and said second stop is coupled with said rotator portion.

4. The proximal adaptor of claim 3 wherein said rotator portion is constructed of translucent material thereby providing a visual indication of the relative displacement of said translational element along said threaded element.

5. The proximal adaptor of claim 4 wherein the translational element is constructed of a fluorescent colored material.

6. The proximal adaptor of claim 3 wherein the translational element has a hexagonally shaped perimeter surface.

7. A proximal adaptor for steerable catheter systems containing a catheter shaft and a guidewire, said guidewire disposed longitudinally within said proximal adaptor and into said catheter shaft, said proximal adapter comprising:
    a stationary portion in fluid-tight connection with said catheter shaft and creating a hydraulic lumen, said stationary portion including a side arm for fluid connection between said hydraulic lumen and an external fluid source;
    a turn limiter section rotatably mounted to said stationary portion, said turn-limiter section comprising:
    a threaded portion rigidly secured to said stationary portion and having a channel along its central longitudinal axis, thread along its outer surface, and a flange extending outwardly from the threaded portion;
    a translational nut disposed on and in threaded communications with the outer surface of said threaded portion allowing longitudinal movement of said nut along said threaded portion by rotating said nut relative to said threaded portion, a rotator portion rotatably secured to said stationary portion and engaging said nut such that said nut rotates in response to rotation of said rotator portion, rotation of said rotator portion thereby causing said nut to travel longitudinally along said threaded portion; and a first stop means positioned at one end of said threaded portion and a second stop means positioned at the opposite end of said threaded portion, said first stop means and said second stop means limiting the longitudinal displacement of said translational nut along said threaded portion.

8. The proximal adaptor of claim 7, wherein the rotator portion is made of translucent material allowing the user to view the rotational movement and longitudinal positioning of said translational nut.

9. The proximal adaptor of claim 7, further comprising an O-ring forming a fluid-tight seal between said stationary portion and said guide wire thereby providing a fluid-tight hydraulic conduit between said catheter shaft and said side arm.

10. The proximal adaptor of claim 9, wherein the translational nut has a hexagonally shaped perimeter surface and said rotator portion has a hexagonally shaped inner surface.

* * * * *